US006350595B1

(12) United States Patent
Neuner

(10) Patent No.: US 6,350,595 B1
(45) Date of Patent: Feb. 26, 2002

(54) SYNTHESIS OF POLYNUCLEOTIDES HAVING RANDOM SEQUENCES

(75) Inventor: Philippe Neuner, Albano Laziale RM (IT)

(73) Assignee: Istituto di Ricerche di Molecolare P. Angeletti S.p.A., Pomezia Rome (IT)

( * ) Notice: Subject to any disclaimer, the term of this patent is extended or adjusted under 35 U.S.C. 154(b) by 0 days.

(21) Appl. No.: 09/530,128

(22) PCT Filed: Oct. 28, 1998

(86) PCT No.: PCT/IT98/00298

§ 371 Date: Apr. 27, 2000

§ 102(e) Date: Apr. 27, 2000

(87) PCT Pub. No.: WO99/21873

PCT Pub. Date: May 6, 1999

(30) Foreign Application Priority Data

Oct. 28, 1997 (IT) ....................... RM97A 0651

(51) Int. Cl.[7] .......................... C12P 19/34; C12P 19/30; C12Q 1/68; G01N 33/00; C07H 21/02

(52) U.S. Cl. ........................... 435/91.1; 435/6; 435/89; 436/94; 536/25.3

(58) Field of Search .................... 435/6, 89, 91.1, 435/183; 436/94; 536/23.1, 24.3, 24.33, 25.3; 702/20

(56) References Cited

U.S. PATENT DOCUMENTS 5,523,388 A 6/1996 Huse ................... 536/22.1
5,629,179 A 5/1997 Mierendorf ............ 435/91.2

FOREIGN PATENT DOCUMENTS

WO 83 02626 8/1983

OTHER PUBLICATIONS

Virnekas et al., Trinucleotide phosphoramidites: ideal reagents for the synthesis of mixed oligonucleotides for random mutagenesis. Nucleic Acids. Res. 22, 5600–5607, 1994.*

Kayushin et al., "A Convenient Approach to the Synthesis of the Trinucleotide Phosphoramidites–Synthons for the Generation of Oligonucleotide," Nucleic Acids Research, vol. 24, No. 19, 1996, pp. 3748–3755.

Altschul et al, "Significance of Nucleotide Sequence Alignments: A Method for Random Sequence Permutation that Preserves Dinucleotide and Codon Usage," Mol. Biol. Evol., vol. 2, No. 6, 1985, pp. 526–538.

* cited by examiner

Primary Examiner—Ethan Whisenant
Assistant Examiner—Frank Lu
(74) Attorney, Agent, or Firm—Joanne M. Giesser; Jack L. Tribble

(57) ABSTRACT

Subject of this invention is a process for the chemical synthesis of polynucleotides having totally or partially random sequences, based on the utilization, as synthesis monomer units for the random sequence part, or presynthesized mononucleotides and dinucleotides. Said synthesis is carried out on separate supports, so that on each of those supports is alternated at least one reaction cycle wherein a mixture of said dinucleotides is bound, with at least one reaction cycle wherein a mononucleotide is bound, and that in a preferred embodiment at the end of the n cycles required for a codon synthesis, the supports are mixed and then redivided into one or more reaction containers. The resulting polynucleotides are such that, for the random sequence part, each trinucleotide unit is fit to match only a limited number of codons, predefined for each unity in number and sequence, and the genetic code degeneracy effects can thus be eliminated. FIG. 1 shows the chemical structure of the dinucleotides utilized as monomer units for the synthesis of codons forming the final sequence.

22 Claims, 1 Drawing Sheet

1.  TG  B2 = T      B1 = $G^{ibu}$
2.  AA  B2 = $A^{bz}$   B1 = $A^{bz}$
3.  GG  B2 = $G^{ibu}$  B1 = $G^{ibu}$
4.  AC  B2 = $A^{bz}$   B1 = $C^{bz}$
5.  CT  B2 = $C^{bz}$   B1 = T
6.  GT  B2 = $G^{ibu}$  B1 = T
7.  TC  B2 = T      B1 = $C^{bz}$
8.  CG  B2 = $C^{bz}$   B1 = $G^{ibu}$
9.  CC  B2 = $C^{bz}$   B1 = $C^{bz}$
10. AG  B2 = $A^{bz}$   B1 = $G^{ibu}$
11. TT  B2 = T      B1 = T ibu = isobutirryl      bz = benzoyl

| | | | |
|---|---|---|---|
| 1. | TG | B2 = T | B1 = $G^{ibu}$ |
| 2. | AA | B2 = $A^{bz}$ | B1 = $A^{bz}$ |
| 3. | GG | B2 = $G^{ibu}$ | B1 = $G^{ibu}$ |
| 4. | AC | B2 = $A^{bz}$ | B1 = $C^{bz}$ |
| 5. | CT | B2 = $C^{bz}$ | B1 = T |
| 6. | GT | B2 = $G^{ibu}$ | B1 = T |
| 7. | TC | B2 = T | B1 = $C^{bz}$ |
| 8. | CG | B2 = $C^{bz}$ | B1 = $G^{ibu}$ |
| 9. | CC | B2 = $C^{bz}$ | B1 = $C^{bz}$ |
| 10. | AG | B2 = $A^{bz}$ | B1 = $G^{ibu}$ |
| 11. | TT | B2 = T | B1 = T | ibu = isobutirryl    bz = benzoyl

SYNTHESIS OF POLYNUCLEOTIDES HAVING RANDOM SEQUENCES

CROSS REFERENCE TO RELATED APPLICATION

The present application is the national stage under 35 U.S.C. 371 of PCT/IT98/00298, filed Oct. 28, 1998, which now is WO 99/21873.

DESCRIPTION

The subject of the present invention is a process for the synthesis of polynucleotides enabling to introduce random sequences along more or less extended tracts of the molecule, in such a way that randomness refers to units of three adjacent nucleotides, and that each one of the said units is fit in so as to match a limited number of codons, predefined in number and sequence, and in order to eliminate the effects of the genetic code degeneracy.

The applicative potentialities of a polynucleotide synthesis process with the above features are undoubtedly remarkable. Indeed, in recent years applications requiring its use have taken on an ever-increasing importance in many fields of the scientific research. It is the case, for instance, of site-specific mutagenesis, operated on a gene coding for a known protein in presumedly key positions in order to verify their actual role in the molecule structure or function. Another example is provided by libraries, containing "boxes" of random sequence synthetic oligonucleotides, that are realized in order to select molecules capable to carry out new biological functions.

In all these cases it is of the utmost importance that the randomness of the sequence is somehow controlled, so that only the desires codons shall be inserted, besides eliminating the effects of the genetic code degeneracy. Of equal importance is, obviously, the fact that said polynucleotide synthesis is carried out with a simple, cost-effective and efficient process.

TERMINOLOGY

It is useful to specify the terms hereinafter:

Support=the term support refers to a solid phase material to which monomers are bound in order to realize a chemical synthesis; said support is usually composed of resin or porous glass grains, but can also be made of any other material known to the man skilled in the art. The term is meant to comprise one or more monomers coupled to the support for the additional reactions of polynucleotides synthesis.

Coniugate or condense: these terms refer to the chemical reactions carried out in order to bind a monomer to a second monomer or to a solid support. These reactions are known to the man skilled in the art and are usually realized in an automated DNA synthetizer, following the instructions provided by the maker.

Monomers or mononucleotides: the terms monomer or mononucleotide refer to individual nucleotides utilized in the chemical synthesis of oligonucleotides. Monomers that can be utilized comprise both ribo- and deoxyribo-forms of each of the five standard nucleotides (derived from the bases adenine (respectively A or dA), guanine (G or dG), cytosine (C or dC), thymine (T) and uranic (U)). Base derivatives or precursors like inosine are also comprised in monomers, as well as chemically modified nucleotides, such as those for instance with a reversible blocking group in any position on the purinic or pyrimidinic bases, on ribose or deoxyribose or on hydroxylic or phosphate groups of the monomer. Those blocking groups comprise e.g. dimethoxytrityl, benzoyl, isobutyryl, beta-cyanoethyl and diisopropylamin groups, and are used to protect hydroxylic groups, phosphates and hexocyclic amines. However, other blocking agents known to the man skilled in the art may be adopted.

Dimers or dinucleotides: the terms dimers or dinucleotides refer to molecular units derived from the condensation of two monomers or mononucleotides as aforespecified.

Synthesis monomeric units: this term indicates unite utilized as essential elements in the synthesis process. In the process subject of the present invention they can consist of monomers or dimers; they can also be constituted of trinucleotide units in other processes known in art.

Codon or triplet: the term codon or triplet refers to a sequence of three adjacent desoxyribonucleotide monomers that specify one of the 20 natural amino acids utilized in a polypeptide biosynthesis. The term comprises also nonsense codons, codons that do not encode any amino acid.

Codon or randomized triplet: these terms refer to the case where the same sequence position corresponds to more than one codon in a polynucleotides set. The number of different codons can vary from 2 to 64 for each specific position.

Anticodon: the term anticodon refers to a sequence of three adjacent ribonucleotidic monomers that specify for a corresponding codon according to the known rule of purinic and pyrimidinic bases coupling.

Polynucleotides or Randomized oligonucleotides: this term refers to a set of oligonucleotides having randomized codons at one or more positions. For example, if the randomized oligonucleotides consist of six nucleotides in length (i.e. two codons), and both the first and the second position of the sequence are randomized so as to code for all of the twenty amino acids, then the population of randomized oligonucleotides shall comprise an oligonucleotide set with every possible combination of the twenty triplets in the first and second position. In this case, therefore, the number of possible codon combinations is 400. Analogously, if 15 nucleotide-long randomized oligonucleotides are synthetized in such a way as to be randomized in every position, then all the triplets coding for each of the twenty amino acids will be found in every position. On this case, the randomized oligonucleotides population shall contain $20^5$ different possible oligonucleotide species.

When not clearly defined, other terms in use in, the present description are meant to be known to men skilled in the field, to whom the invention is aimed at.

For some terms pertaining molecular biology techniques, cfr. the Sambrook et al. manual (Sambrook et al, 1989). Other terms referred to substances of chemical nature not clearly defined are meant to be known to men skilled in field of the invention, and anyhow their definitions can be found in manuals like Gait, M. J. et al, 1984.

STATE OF THE ART

In general, applications that utilize synthetic oligonucleotides are of two kinds: those requiring the use of known sequence oligonucleotides, and those requiring the use of oligonucleotides with an at least partly degenerated or random sequence.

As for the first group of applications, the usual synthesis methods are based on the principle of building the polynucleotide condensing mononucleotides one at the time, starting from the first at the 3'-terminus, and choosing each mononucleotide for every reaction cycle so as to synthetize a polynucleotide with a desired and unambiguous sequence.

As for the second group of applications, the synthesis follows the same modalities, but in the positions along the sequence where one needs to insert variability the synthetic cycle goes on using mixtures of two or more different monomers. In every cycle oligonucleotide mixtures differing in the monomer added to the 5'-terminus are thus created. For instance, if in a cycle 4 different mononucleotides are employed as monomers, a mixture containing 4 different polynucleotides differing among themselves only for the last nucleotide inserted is obtained. If a synthetic cycle of the same kind is repeated, a mixture of 16 polynucleotides that differ in the last two inserted nucleotides is obtained, and so on.

In general, applications utilizing synthetic polynucleotides provide for a direct or indirect insertion of said polynucleotides in genetic material that will be translated into polypeptides in a certain living organism (in vitro translation seldom occurs). As it is known, DNA-translating genetic code is partly degenerated, i.e. as the 64 possible codons formed by groups of three nucleotides code for 20 amino acids only (plus three terminating or stop signals), more than one codon code for a single amino acid.

Oligonucleotides having an at least partly random sequence as aforedescribed (where for random sequence polynucleotide is meant a more or less complex mixture of polynucleotides having different sequences), code for random sequence peptides (i.e. for a mixture of peptides, each peptide being coded by one or more polynucleotides).

In fact, genetic code degeneracy entails three important consequences on the random sequence oligonucleotides that are to be used for the random polypeptides derivation:

a) any mixture of oligonlicleotides having an at least partly random sequence, codes for a much simpler polypeptide mixture. For instance, a mixture of oligonucleotides wherein 6 positions are randomly filled by one of the four natural nucleotides is made of 4096 different molecules ($4^6$ if single nucleotides are considered, or $64^2$ if codons are considered), but exactly by virtue of the code degeneracy, these code only for 400 different polypeptides (i.e. $20^2$).

This phenomenon would be irrelevant by itself, provided that the different polynucleotides that code for the polypeptide had the same physical and chemical features, but different sequences can confer different properties concerning for example solubility, stability and static charge in different conditions, adsorption with filtering means and so on.

b) in the mixture of polypeptides originated by random sequence polynucleotides translation, there will be a percentage of truncated sequence peptides. As a matter of fact, during the random incorporation of the codons also those indicating a stop signal are necessarily inserted, and truncated sequence polypeptides formation is therefore unavoidable.

In the preceeding example, out of 4096 oligonucleotides, 375 (9%) will code for polypeptides truncated at the first or second position (i.e. 3 possible termination codons at the first position for each of the 64 possible codons at the second position, and 3 possible stop codons at the second for each of the 61 possible codons at the first). Therefore, together with 400 possible polypeptides, 21 truncated polypeptides will be found (one at the first position and 20 at the second position). This phenomenon acquires a particular significance when libraries of polynucleotides possessing a longish random sequence are created. For instance, in a 27-nucleotides library (coding for nonapeptides libraries, as described in many applications) as much as 35% of the polynucleotides contain a stop codon (or $[64^9-61^9]/64^9$). Longer sequences will contain a higher percentage of molecules coding for a premature termination of the polypeptide chain.

c) The existence of a dissimilar translating efficiency of the different codons coding for the same amino acid in different organisms, becomes evident in the derivation of polypeptide mixtures with complexities different from that of the starting polynucleotide mixtures. Although the genetic code is unique in nature, as a matter of fact, there is a difference in the various living organisms in the efficiency with which different codons coding for the same amino acid are translated. For instance, in *E. Coli* serin is coded 18 times more by codon UCU than by codon UCA. It follows that two different polynucleotides at equimolar concentration into the initial mixture will be translated with different efficiency, and the resulting polypeptide mixture will contain a different molar ratio of the two molecular species. It is of the utmost relevance therefore, in order to maximize the efficiency of the selected cellular system, that the coding sequences contain the very codons that are primarily utilized by the cellular system itself.

All three of these factors exert a strong influence on the efficiency of systems that utilize random sequence polynucleotides, both in applications that provide for the randomization in just one position, and in applications whose randomization refers to longer sequences. This influence however, is directly proportional to the length and complexity of the random sequence adopted.

This fact interferes especially with the preparation of completely homogeneous mixtures (i.e. those containing the same concentration of every possible molecular species) of random sequence polynucleotides, finalized to the preparation of equally complex and homogeneous polypeptide mixtures. Actually, every effort in this direction is partly thwarted when translating polynucleotides in polypeptide molecules, exactly because of the combination of those three factors, and that cannot possibly leave unaffected a considerable series of applications.

Such is the case for example of the efficiency of expression libraries created with such a homogeneous mixture of polynucleotides.

In connection with all these problems, synthesis processes were developed over time aimed at their overcoming and at the efficiency improvement of the various systems that utilize random sequence polypeptides.

A first solution (perhaps the most obvious from a theoretical point of view) is a polynucleotide synthesis that provides for the utilization as monomeric units of preformed trinucleotides (corresponding to codons), instead of the individual mononucleotides (Virkenas, B. et al, 1994; Lyttle, M. U. et al, 1995; Ono, A. et al, 1994). Thus the 20 trimers corresponding to the desired codons can first be synthetized, and polynucleotide synthesis is carried out only later by condensing at each synthesis cycle the monomeric units made of trimers instead of monomers. This solution is apparently simple and effective, but actually requires a complex, expensive and inefficient process, for the reasons hereinafter:

1. Although the initial trinucleotides synthesis is easily achievable by the condensing of three blocked nucleotides carried out in accordance with the regular polynucleotide synthesis process (therefore by a relatively simple and efficient process), there is a number of problems strictly inherent to the detaching phase of the newly formed trinucleotide from the synthesis matrix.

Actually, in the normal processes this operation is concurrent to the lysis of all the groups protecting the various bases, but in this case, as in view of the subsequent use in polynucleotide synthesis the bond between nucleotides and lateral protective groups must remain intact, attempts were made to allow the lysis of the 3'-5' bond with the support matrix without involving bonds with lateral protective groups.

From this the necessity of using unusual protective groups and of having to reckon with production yields varying from one codon to another, hardly reproducible and in any case low.

Completely analogous difficulties arise when the synthesis is carried out in solution, rather than on resin. In this case as well, the individual trinucleotides need to be selectively unblocked before use, exclusively at 3' position (in order to make them reactive), while all other functions muse remain blocked.

2. In the normal synthesis of random sequence polynucleotides, based on mononucleotides use, in each synthesis cycle a mixture composed of at least two nucleotides is used. In the knottiest chemical condition, all 4 possible nucleotides are used, but even if each of them possesses a reactivity slightly different from the others, there being only 4 components, the optimal molar ratio conditions that will foster the equimolar incorporation of each nucleotide in the forming polynucleotide chain are not difficult to find.

Of much greater importance are the difficulties one finds when as many as 20 different trinucleotides have to be incorporated in an equimolar quantity. Firstly, the fact that among all possible trinucleotides there exists a difference in the relative chemical reactivity, markedly greater than that among the four simple mononucleotides, has to be reckoned with.

Moreover, while nucleotides are easily available in pure form and with a controlled and reproducible reactivity, trinucleotides, for the aforementioned difficulties, will be available in solutions whose qualitative and quantitative content is not easily verifiable. Lastly, it will be obviously difficult to find the right molar ratios of the 20 components forming the synthesis mixture, sufficient to grant an equimolar incorporation. Of course all these difficulties are minimized by the adoption of less complex mixtures.

A second approach, much simpler from the point of view of chemical synthesis, is based on the fact that when more codons code just for one amino acid, the first two codon bases are often constant, differing only in the third codon base.

The difference among codons represented in the polynucleotide can therefore be reduced if, during the synthesis of each trinucleotide unit, In the first cycle (that will give the 3'-terminus nucleotide, i.e. the third in codon) a mixture of guanine and thymine (or uracil)-derived nucleotides is used, while in the two condensing cycles hereinafter mixtures of the four mononucleotides are used. Thus, polynucleotides are synthetized that may not contain 64 possible codons but only the degenerated 32 of the kind NNK, where N is any one of the four nucleosides, and K is guanosine or thymidine. It follows that of the 20 coded amino acids, 12 are coded by only one codon, 5 are coded by two possible codons and 3 are coded by three possible codons. Finally, only one codon out of 32 codes for a stop signal.

This method, if compared to the usual synthesis methods, holds the remarkable advantage of requiring no change whatsoever, but does not solve if not partially the aforediscussed problems. Specifically, although in comparison to the usual methods it gives a partial solution, does not solve the problem of the stop codons introduction, and of the resulting formation of truncated polypeptides. (Huang, W. e Santi, D. V., 1994).

Another method described in the art is based on the principle of subdividing the synthesis support in as many synthesis containers (usually columns), as the different codons that will be inserted in a predetermined position in the oligonucleotide are. Single codons are then synthetized on every support, and the various supports are then mixtured in order to obtain a randomized polynucleotide mixture (U.S. Pat. No. 5,523,388). For instance, if four codons coding for four amino acids have to be inserted in a predetermined position, synthesis resin is subdivided in four portions, the first codon is synthetized on the first one, the second codon on the second one, and so on. Once the synthesis has ended the four supports are mixtured, thus obtaining a support resin that bears a conjugated polynucleotide whose 5' terminal codon is randomized for the four codons.

This method has the advantage of allowing an exact selection of the codons that have to be inserted in a predetermined position. Its main limitation derives from the necessity of having to redivide the synthesis resin in as many portions as the desired codons are. Synthesis becomes then relatively simple if the number of codons is small but extremely complex if it is high, when up to twenty different synthesis supports must be prepared for every position intended for randomization. As it is necessary to work with relatively small amount of resin in order to contain production costs, therefore it becomes extremely cumbersome to subdivide the resin in 10 or more different amounts difficult to handle in the complicated operations of chemical reactions and washings needed in every synthesis cycle. Moreover, it must be noted that the synthesis scale cannot be increased by more than a few micromoles (about 10–15 micromoles) without running into considerable efficiency losses of the coupling reactions.

SUMMARY OF THE INVENTION

The present invention aims at overcoming the aforementioned difficulties by a process ensuring at the same time a-remarkable simplicity and cost-effectiveness in the synthesis. The invention is based on the observation that every trinucleotide composing a codon can be considered as constituted of a monoucleotide and of a dinucleotide that follows it or comes first in the sequence.

The distinctive features of this approach can be evidenced by a simple comparison of the codons shown in the usual way (table I), with the same shown to point out the mononucleotide-dinucleotide (table II) and dinucleotide-mononucleotide (table III) combinations.

TABLE I genetic code

|  |  | Second position |  |  |  |  |
|---|---|---|---|---|---|---|
|  |  | T | C | A | G |  |
| First position (5'end) | T | TTT Phe F | TCT Ser S | TAT Tyr Y | TGT Cys C | T Third position (3'end) |
|  | T | TTC Phe F | TCC Ser S | TAC Tyr Y | TGC Cys C | C |
|  | T | TTA Leu L | TCA Ser S | TAA STOP | TGA STOP | A |
|  | T | TTG Leu L | TCG Ser S | TAG STOP | TGG Trp W | G |
|  | C | CTT Leu L | CCT Pro P | CAT His H | CGT Arg R | T |
|  | C | CTC Leu L | CCC Pro P | CAC His H | CGC Arg R | C |
|  | C | CTA Leu L | CCA Pro P | CAA Gln Q | CGA Arg R | A |
|  | C | CTG Leu L | CCG Pro P | CAG Gln Q | CGG Arg R | G |
|  | A | ATT Ile I | ACT Thr T | AAT Asn N | AGT Ser S | T |
|  | A | ATC Ile I | ACC Thr T | AAC Asn N | AGC Ser S | C |
|  | A | ATA Ile I | ACA Thr T | AAA Lys K | AGA Arg R | A |
|  | A | ATG Met M | ACG Thr T | AAG Lys K | AGG Arg R | G |
|  | G | GTT Val V | GCT Ala A | GAT Asp D | GGT Gly G | T |
|  | G | GTC Val V | GCC Ala A | GAC Asp D | GGC Gly G | C |
|  | G | GTA Val V | GCA Ala A | GAA Glu E | GGA Gly G | A |
|  | G | GTG Val V | GCG Ala A | GAG Glu E | GGG Gly G | G |

TABLE II

B + D combination

B = First postion (5' end)

| T | C | A | G | D dinucleotide (3' end) |
|---|---|---|---|---|
| TTT Phe F | CTT Leu L | ATT Ile I | GTT Val V | TT |
| TTC Phe F | CTC Leu L | ATC Ile I | GTC Val V | TC |
| TTA Leu L | CTA Leu L | ATA Ile I | GTA Val V | TA |
| TTG Leu L | CTG Leu L | ATG Met M | GTG Val V | TG |
| TCT Ser S | CCT Pro P | ACT Thr T | GCT Ala A | CT |
| TCC Ser S | CCC Pro P | ACC Thr T | GCC Ala A | CC |
| TCA Ser S | CCA Pro P | ACA Thr T | GCA Ala A | CA |
| TCG Ser S | CCG Pro P | ACG Thr T | GCG Ala A | CG |
| TAT Tyr Y | CAT His H | AAT Asn N | GAT Asp D | AT |
| TAC Tyr Y | CAC His H | AAC Asn N | GAC Asp D | AC |
| TAA STOP | CAA Gln Q | AAA Lys K | GAA Glu E | AA |
| TAG STOP | CAG Gln Q | AAG Lys K | GAG Glu E | AG |
| TGT Cys C | CGT Arg R | AGT Ser S | GGT Gly G | GT |
| TGC Cys C | CGC Arg R | AGC Ser S | GGC Gly G | GC |
| TGA STOP | CGA Arg R | AGA Arg R | GGA Gly G | GA |
| TGG Trp W | CGG Arg R | AGG Arg R | GGG Gly G | GG |

TABLE III

D + B combination

B = First postion (3' end)

| D (5' end) dinucleotide | T | C | A | G |
|---|---|---|---|---|
| TT | TTT Phe F | TTC Phe F | TTA Leu L | TTG Leu L |
| TC | TCT Ser S | TCC Ser S | TCA Ser S | TCG Ser S |
| TA | TAT Tyr Y | TAC Tyr Y | TAA STOP | TAG STOP |
| TG | TGT Cys C | TGC Cys C | TGA STOP | TGG Trp W |
| CT | CTT Leu L | CTC Leu L | CTA Leu L | CTG Leu L |
| CC | CCT Pro P | CCC Pro P | CCA Pro P | CCG Pro P |
| CA | CAT His H | CAC His H | CAA Gln Q | CAG Gln Q |
| CG | CGT Arg R | CGC Arg R | CGA Arg R | CGG Arg R |
| AT | ATT Ile I | ATC Ile I | ATA Ile I | ATG Met M |
| AC | ACT Thr T | ACC Thr T | ACA Thr T | ACG Thr T |
| AA | AAT Asn N | AAC Asn N | AAA Lys K | AAG Lys K |
| AG | AGT Ser S | AGC Ser S | AGA Arg R | AGG Arg R |
| GT | GTT Val V | GTC Val V | GTA Val V | GTG Val V |
| GC | GCT Ala A | GCC Ala V | GCA Ala A | GCG Ala A |
| GA | GAT Asp D | GAC Asp D | GAA Glu E | GAG Glu E |
| GG | GGT Gly G | GGC Gly G | GGA Gly G | GGG Gly G |

In Table II specifically, each codon is shown as resulting from the combination of the first nucleotide plus one dinucleotide (hereinafter referred to also as B+D, where for B the single nucleotide is meant, and for D the dinucleotide), while Table III (also derived from I) represents codons as derived from dinucleotides this time corresponding to the first and second codon base, plus a single nucleotide corresponding to the third base (hereinafter referred to also as D+B, in accordance with the terminology adopted earlier).

A thorough examination of both these alternative representations of the genetic code, enabled the inventor to observe that in comparison to other approaches, the minimum number of monomeric units (constituted by dinucleotides) needed to code for all of the amino acids can be consistently reduced. As a matter of fact, according to the representation D+B, it is equivalent to the 13 dinucleotides (highlighted by hatching in Table III), a very low number that drops even lower at 7 (also highlighted by hatching in table II), if the B+D code representation is followed. The B+D combination must therefore be considered as the most favourable one.

Furthermore, other combinations can be obtained from Tables II and III that, though being overall less favourable than the D+B combination, by virtue of their low number of needed dinucleotides present nevertheless the advantage of allowing the introduction in the sequence of codons favoured in the genetic expression in different organisms. On the basis of the present knowledge in the differential use of the various codons in E. Coli, yeasts and eucaryotic cells, always keeping minimal the number of dimers needed for each synthesis mixture formation (for the detailed description of the invention see infra), it is possible to derive, from Table II, Tables IV, V and VI respectively, wherein usage frequences of the single codons are shown, while the most convenient selections are highlighted by hatching.

TABLE IV combination B + D, applied to E. coli

First postion (5' end)

| T | C | A | G | D dinucleotide (3' end) |
|---|---|---|---|---|
| 24 TTT Phe F | 4 CTT Leu L | 17 ATT Ile I | 51 GTT Val V | TT |
| 76 TTC Phe F | 7 CTC Leu L | 83 ATC Ile I | 7 GTC Val V | TC |
| 2 TTA Leu L | 0 CTA Leu L | 0 ATA Ile I | 26 GTA Val V | TA |
| 3 TTG Leu L | 83 CTG Leu L | 100 ATG Met M | 16 GTG Val V | TG |
| 34 TCT Ser S | 8 CCT Pro P | 35 ACT Thr T | 35 GCT Ala A | CT |
| 37 TCC Ser S | 0 CCC Pro P | 55 ACC Thr T | 10 GCC Ala A | CC |
| 2 TCA Ser S | 15 CCA Pro P | 4 ACA Thr T | 28 GCA Ala A | CA |
| 3 TCG Ser S | 77 CCG Pro P | 7 ACG Thr T | 26 GCG Ala A | CG |
| 25 TAT Tyr Y | 17 CAT His H | 6 AAT Asn N | 33 GAT Asp D | AT |
| 75 TAC Tyr Y | 83 CAC His H | 94 AAC Asn N | 67 GAC Asp D | AC |
| 0 TAA STOP | 14 CAA Gln Q | 74 AAA Lys K | 78 GAA Glu E | AA |
| 0 TAG STOP | 86 CAG Gln Q | 26 AAG Lys K | 22 GAG Glu E | AG |
| 49 TGT Cys C | 74 CGT Arg R | 3 AGT Ser S | 59 GGT Gly G | GT |
| 51 TGC Cys C | 25 CGC Arg R | 20 AGC Ser S | 38 GGC Gly G | GC |
| 0 TGA STOP | 1 CGA Arg R | 0 AGA Arg R | 0 GGA Gly G | GA |
| 100 TGG Trp W | 0 CGG Arg R | 0 AGG Arg R | 2 GGG Gly G | GG |
| Z | X | W | Y | |

TABLE V combination B + D applied to Yeast

First postion (5' end)

| T | C | A | G | D dinucleotide (3' end) |
|---|---|---|---|---|
| 27 TTT Phe F | 3 CTT Leu L | 52 ATT Ile I | 56 GTT Val V | TT |
| 73 TTC Phe F | 0 CTC Leu L | 46 ATC Ile I | 37 GTC Val V | TC |
| 18 TTA Leu L | 7 CTA Leu L | 2 ATA Ile I | 3 GTA Val V | TA |
| 69 TTG Leu L | 2 CTG Leu L | 100 ATG Met M | 4 GTG Val V | TG |
| 52 TCT Ser S | 18 CCT Pro P | 50 ACT Thr T | 65 GCT Ala A | CT |
| 33 TCC Ser S | 2 CCC Pro P | 43 ACC Thr T | 28 GCC Ala A | CC |
| 6 TCA Ser S | 80 CCA Pro P | 6 ACA Thr T | 6 GCA Ala A | CA |
| 1 TCG Ser S | 1 CCG Pro P | 1 ACG Thr T | 1 GCG Ala A | CG |
| 19 TAT Tyr Y | 35 CAT His H | 22 AAT Asn N | 52 GAT Asp D | AT |
| 81 TAC Tyr Y | 65 CAC His H | 78 AAC Asn N | 48 GAC Asp D | AC |
| 80 TAA STOP | 95 CAA Gln Q | 22 AAA Lys K | 90 GAA Glu E | AA |
| 10 TAG STOP | 5 CAG Gln Q | 78 AAG Lys K | 10 GAG Glu E | AG |
| 89 TGT Cys C | 15 CGT Arg R | 5 AGT Ser S | 91 GGT Gly G | GT |
| 11 TGC Cys C | 0 CGC Arg R | 4 AGC Ser S | 6 GGC Gly G | GC |
| 9 TGA STOP | 0 CGA Arg R | 83 AGA Arg R | 2 GGA Gly G | GA |
| 100 TGG Trp W | 0 CGG Arg R | 1 AGG Arg R | 1 GGG Gly G | GG |

TABLE VI genetic code base + dimer according to the most frequent codons in eucaryotes First postion (5' end)

| T | C | A | G | D dinucleotide (3' end) |
|---|---|---|---|---|
| 20 TTT Phe F | 5 CTT Leu L | 18 ATT Ile I | 75 GTT Val V | TT |
| 30 TTC Phe F | 26 CTC Leu L | 77 ATC Ile I | 25 GTC Val V | TC |
| 2 TTA Leu L | 3 CTA Leu L | 5 ATA Ile I | 5 GTA Val V | TA |
| 6 TTG Leu L | 58 CTG Leu L | 100 ATG Met M | 64 GTG Val V | TG |
| 13 TCT Ser S | 19 CCT Pro P | 14 ACT Thr T | 17 GCT Ala A | CT |
| 28 TCC Ser S | 48 CCC Pro P | 57 ACC Thr T | 53 GCC Ala A | CC |
| 5 TCA Ser S | 16 CCA Pro P | 14 ACA Thr T | 13 GCA Ala A | CA |
| 9 TCG Ser S | 17 CCG Pro P | 15 ACG Thr T | 17 GCG Ala A | CG |
| 26 TAT Tyr Y | 21 CAT His H | 22 AAT Asn N | 25 GAT Asp D | AT |
| 74 TAC Tyr Y | 79 CAC His H | 78 AAC Asn N | 75 GAC Asp D | AC |
| 23 TAA STOP | 12 CAA Gln Q | 18 AAA Lys K | 25 GAA Glu E | AA |
| 21 TAG STOP | 88 CAG Gln Q | 82 AAG Lys K | 75 GAG Glu E | AG |
| 32 TGT Cys C | 7 CGT Arg R | 10 AGT Ser S | 12 GGT Gly G | GT |
| 68 TGC Cys C | 37 CGC Arg R | 34 AGC Ser S | 50 GGC Gly G | GC |
| 55 TGA STOP | 6 CGA Arg R | 10 AGA Arg R | 14 GGA Gly G | GA |
| 100 TGG Trp W | 21 CGG Arg R | 18 AGG Arg R | 24 GGG Gly G | GG |

The chemical synthesis process is organized consequently to the selected combination. In accordance with the features of the selected approach, the process proposed as preferred is the one based on the nucleotide-dinucleotides combination shown in Table II (i.e. the B+D one) described hereinafter.

The process provides for the preparation of 4 identical synthesis columns, containing the common resin used for this purpose, marked with the names of the four nucleotides, i.e. T (or U where a polyribonucleotide is to be synthetized), C, A, G. Then a mixture of opportunely selected dinucleotides is condensed on the resin inside an automated synthetizer. In the first column (T) the mixture is constituted by the dinucleotides that in Table II are hatched correspondingly (TT; CT; AT; GT; GG). In the second column (C) the mixture is constituted by the dinucleotides that in Table II are hatched correspondingly (TT; CT; AT; AA; GT). In the third column (A) the mixture is constituted by the dinucleotides that in Table II are hatched correspondingly (TT; TG; CT; AT; AA). In the fourth (G) the mixture is constituted by the dinucleotides that in Table II are hatched correspondingly (TT; CT; AT; AA; GT). To this synthesis cycle there follows a second cycle, where a single nucleotide (and specifically the one shown with the symbol of the column, i.e. T in the first, C in the second, A in the third and G in the fourth) is additioned to each column. At the end of the second cycle, all twenty of the preselected codons will have been inserted in the resin of the four columns, but in each column will be present only the codons hatched in Table II. In order to further randomize the sequence, the columns are now opened, the synthesis resin is recovered and the four resins are carefully mixtured.

The mixtured resin is redistributed into four columns, the columns are reconnected to the synthesis apparatus, and the two synthesis cycles are repeated as aforedescribed. In practice, in every double synthesis cycle three new units are added to the forming polynucleotide chain in order to form only the preselected codons, but in a totally random way, i.e. regardless of the selected codons.

This synthetic method presents remarkable advantages relative over those described in the state of the art, that are summed up hereinafter.

Dinucleotide synthesis is carried out by methods that are well described in literature, therefore by using low-cost, commercially available reagents, in solution and with product yields of 85–90% (Kumar, G. 1984).

In most cases difference in the reactivity of different dinucleotides is expected to be inferior to reactivity differences peculiar instead of trinucleotides. The main consequence is that homogeneous incorporations in the forming polynucleotide chain of all molecular species present in the synthesis mixture are easier to obtain. Reagents purity is a determining factor for this aspect of the reaction.

The total number of dinucleotides required to cover all possible combinations is extremely low. Actually, it varies from a minimum of 7 to a maximum of 20, and in the more usual cases, as for those described herein, 11 dimers are sufficient.

The selection of dinucleotides to be used can be done so as to minimize the number of molecular species forming the synthesis mixture. An example is that shown in Table II, where dimers were selected so that each synthesis mixture contains only 5 dinucleotides. This makes the search for suitable reaction conditions and for relative molar concentrations of the reagents much easier, in order to optimize the homogeneous incorporation of all components.

A synthesis carried out according to this approach, enables to incorporate complete codons in the forming chain. In fact, a careful selection of dinucleotides and mononucleosides, enables to direct the synthesis so to leave out undesired codons such as stop codons. A combination specifically excluding only stop codons is for instance the one shown in Table II, but it is also possible to modify the combination so as to leave out, in one or more positions of the final sequence, any undesired codon.

If for example some amino acids were to be left off from a certain position of the polypeptidic chain, for instance the acid ones (glutamic acid, Glu or E, and aspartic acid, Asp o D), leaving out of the mixture applied to column G at the synthesis cycle corresponding to the desired position dimers AT and AA would suffice. However, according to the same principle, other countless combinations are possible.

In relation to each amino acid synthesis, the possibility of selecting a suitable codon among the many possible ones allows the insertion of only those codons that are preferentially used in the proteinic synthesis of the selected microorganism. Therefore, by leaving out of the random sequence oligonucleotide mixture those translated in the system with a lesser efficiency, it is possible to maximize genetic expression, thus obtaining a better correspondence between the homogeneities of the oligonucleotide and of the resulting oligopeptide mixture.

All these considerations highlight the remarkable advantages deriving from such an approach As a matter of fact, they do not pertain exclusively to the process based on a B+D combination, on the contrary they are valid for any kind of process deriving from the general approach and therefore inferable from the aforementioned one.

In fact, for instance on the basis of the combination shown in Table III, it is possible to infer a synthesis process differing from the preceeding one only for the aspect that the order of the two synthetic cycles must be inverted: first of all single mononucleotides are condensed on synthesis resins, and dinucleotide mixtures only in the second round.

This second process, like the others deriving from further possible combinations, although comprised in the intentions of the inventor, shall not be specified further, because those are essentially inferable from the first process aforedescribed.

DESCRIPTION OF THE FIGURES

The invention will be better clarified with the aid of the annexed FIG. 1.

DETAILED DESCRIPTION OF THE INVENTION

Figure 1:
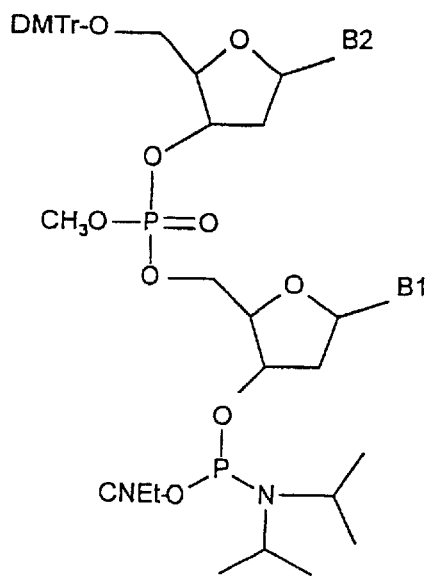
FIG. 1 shows the chemical structure of the dimers utilized as monomeric units in the synthesis of final sequence codons. Each dimer is obtained by substituting groups in B2 and then in B1 position, as specified for each dimer.

A process is described for the synthesis of oligonucleotide mixtures that contain totally or partially randomized nucleotide sequences and that have the following features:
 each mixture component codes for a different polypeptide different oligonucleotides coding for the same polypeptide are not present in the mixture;
 the random sequence part inserted in each mixture component is composed in such a way that sequence randomness refers to a unit of three adjacent nucleotides (usually corresponding to a codon) instead of single nucleotides.

The random sequence part inserted in each mixture component is in fact composed in such a way that, considering three adjacent nucleotides units, each unit may adopt the sequence of a limited number of trinucleotides, defined in a predetermined list, and containing from two to 64 of the possible trinucleotides formed by the combination of the four natural mononucleotides.

These features are a direct consequence of the synthesis process. In its preferred form, this is based on the following operations:
 a) preselection of dinucleotides in groups, each group consisting in those dinucleotides constituting the second and the third base of at least one of the codons desired in the sequence shaking the first base.
 b) preparation of mixtures containing activated dinucleotides, said dinucleotides being redistributed in said mixtures as well as grouped by the operation of which under a) in a suitable concentration in order to obtain homogeneity in the corresponding triplets representation;
 c) synthesis that can be carried out in parallel or not, on one or more reaction containers holding a support for the solid phase synthesis of a known sequence that will result-on the 3'-terminus of the final sequence;
 d) addition of the activated dinucleotides mixtures of which under b) in the synthesis containers, one for each container, and ensuing binding reaction of the activated dinucleotides thereby contained, with the 5'-terminus of the synthetized sequences of which under c);
 e) addition of at least one mononucleotide to at least one of the synthesis containers, one mononucleotide for each container, and ensuing binding reaction at the 5'-terminus of said dinucleotides thereof.
 f) opening of the container and mixturing of the supports in order to obtain a homogeneous reaction mixture;
 g) reconstitution of the synthesis containers with an amount of homogeneous mixture of which in the preceding item g) equal to a 1/n fraction for each container, where n is the number of containers used;
 h) repetition of the operational sequence under d), e), f), and g) as many times as needed by the
 i) synthesis on the containers in parallel or not of a known sequence that will be at the 5'-terminus of the final polynucleotide product.

In order to exemplify the ways of performing the various operations aforementioned, the process is summarized hereinafter, therefore each step may be reworked (or fragmented if needle be) on the basis of applicative criteria more commonly adopted in laboratory practice.

The process can therefore be realized as follows:
 α. a table of the 64 trinucleotides, obtainable taking into account the combination of each of the 4 possible nucleotides with each of the 16 possible dinucleotides (as for example in Table II)
 β. Next to each trinucleotide listed in the table are noted the features to consider in the use of the polynucleotide to be synthetized. In its most common (but not unique) form, these features are the amino acids coded accordingly to the natural genetic code, and the trinucleotide relative abundance in natural polynucleotide sequences of organisms wherein the polynucleotide that is to be synthetized shall finally be expressed (as in Tables IV; V and VI). Should it prove possible to establish other peculiar features inherent to trinucleotides, these could be taken into account for the selection of a synthesis strategy.
 γ. A selection of desired trinucleotides is then carried out trying to keep to a bare minimum the number of dinucleotides needed for their synthesis, and so as to have them distributing as uniformly as possible in the four columns of the table (as exemplified by hatchings in Tables II, III, IV, V and VI)
 δ. Preparation of the selected dimers in an activated and protected form. In a preferred embodiment, the present invention provides for the preparation of the dinucleotides needed as described by Kumar G. and Poonian (Kumar G. and Poonian M. S. J. Org. Chem. (1984), Vol 49, pp 4905–4912). Dimers thus obtained are protected at their 5'-terminus by a dimethoxy-trityl group, while the 3'-terminus of the dimer is derivatized with cyanoethylphosphoramidite. Bases are protected with the protecting groups described in art, and in use in oligonucleotide synthesis according to the phosphoramidite method (as in example, not limiting, shown in FIG. 1). Dimer purity is of 85–90%, as determined by Thin Layer Chromatography (TLC) and Nuclear Magnetic Resonance carried out with phosphorus[31] (31P-NMR). To define the scope of this invention, the synthesis methods of the various dimers are unimportant, as long as they are compatible with the condensing method on solid matrix utilized for polynucleotide synthesis.

ε. In the preferred embodiment polynucleotide synthesis is carried out in parallel, utilizing as synthesis containers 4 chromatographic columns for the solid phase synthesis containing resin as a support, adopting usual protocols described from the maker of the apparatus used. Anyway, in the present patent methodologies referring by way of example to the Perkin Elmer firm are described, but it is equally possible to utilize any other set or solid phase synthesis method based on the same or similar enough chemical reactions.

Four synthesis columns are then linked to the set and usually (but not necessarily) utilized for the parallel synthesis of a 3'-terminus portion having a single and defined sequence. In it are often comprised cleavage sites for the restriction enzymes, or any other sequence useful for the cloning, or for any other desirable application of the polynucleotide whatsoever, ζ. Then on columns 1, 2, 3 and 4 (also named T, C, A and G according to the mononucleotide that shall be added later on) respectively the dinucleotide mixtures corresponding to T, C, A and G are additioned for the definition of the codons as specified in the reference Table selected (e.g. one of the tables II, IV, V, VI or even others, prepared as precedingly described in α, β and γ of the present section). The mixture containing dinucleotides corresponding to T shall be denominated mixture T, the one corresponding to A mixture A and so on.

The molar composition of the various mixtures, as well as the coupling times, must be optimized according to circumstances.

In usual practice, coupling times are selected in the range of 20 seconds to 8 minutes, while relative molar concentrations of single dinucleotides present in mixtures can diverge from equimolarity to take into account both the single dinucleotides purity and reactivity thereof. Indications on single dinucleotides reactivity may be inferred from the reactivity of the trinucleotides having the same 3'-terminus dinucleotide as discussed in Virnekas et al. (Virnekas et al, 1994); Ono et al. (Ono et al, 1994); Kagushin et al. (Kagushin et al, 1994).

The dimers condensing reaction generally occurs with a 90–95% yield, measured with trityl release.

η. The next synthesis step consists in the coupling of each monomer to the corresponding column and mixturing as described hereinafter:

Column 1 (mixture T) 5'-O-dimethoxytrityl, thymidine, 3'-O-cyanoethyl phosphoramidite Column 2 (mixture C) 5'-O-dimethoxytrityl, deoxycytidine N4-benzoyl 3'-O-cyanoethyl phosphoramidite Column 3 (mixture A) 5'-O-dimethoxytrityl, deoxyadenosine N6-benzoyl 3'-O-cyanoethyl phosphoramidite Column 4 (mixture G) 5'-O-dimethoxytrityl monomer, deoxyguanosine N2-isobutyryl 3'-O-cyanoethyl phosphoramidite After the usual acetylation of the sequences that did not react, and the oxidation of the internucleotide phosphoric bridge (in accordance with the classical synthesis steps), the synthesis is stopped.

θ. The four synthesis columns are opened and their resins mixtured in order to obtain a homogeneous mixture.

ι. The four synthesis columns are reconstituted with an equivalent amount of resin per column, and the columns are reconnected to the synthetizer.

κ. The process from ζ to ι is repeated as many times as requested by the number of random type trinucleotides that will be inserted in the polynucleoside.

λ. The synthesis is usually terminated synthetizing in parallel on the four columns a polynucleotide 5'-terminus tail of determined sequence, possessing functions analogous to the 3'-terminus sequence discussed in ε.

Therefore, keeping in mind every thing exposed, the subject of the present invention is a process for the chemical synthesis of polynucleotides having a totally or partially random sequence, so that for the random sequence part each trinucleotide unit corresponding to a codon may assume a limited number of predefined sequences. The process is characterized by the fact of utilizing as monomeric units of the random sequence part synthesis presynthetized mononucleotides and dinucleotides, and by the fact that said synthesis is carried out on a multiplicity of supports, so that on each of said supports is alternated at least one reaction cycle wherein a mixture of said dinucleotides is bound, with at least one reaction cycle wherein a mononucleotide is bound. In a preferred embodiment, at the end of the n reaction cycles needed for a codon synthesis supports are mixtured and then redivided into two or more reaction containers.

In particular, the case considered is that or dinucleotides making up the second and the third base, or the first and second base of those codons that share respectively the first or the third base.

Further, the cases considered are the ones wherein such polynucleotides are constituted or deoxyribonucleotides as well as the one wherein they are made of ribonucleotides.

When dinucleotides corresponding to the second and the third base of those codons that share the first base (corresponding to the B+D structure, as seen in the preferred embodiment) are utilized, the process is the one extensively aforeexplained in the operations from a) to i)

In the analogous case wherein are utilized the dinucleotides corresponding to the first and second base of those codons that share the third base (corresponding to the D+B scheme) the process is almost completely identical, but for an inversion of the operations of which in d) and in e).

Particular cases occur when said synthesis is carried out in parallel, and when mixtures are in number of four, the supports are constituted of resin, and the containers constituted of columns.

Subject of the present invention is also the process utilizing dinucleotides that determine the formation of trinucleotide units corresponding to the most frequent codons in *E. Coli*, eucharyotes and yeast genoma, and specifically, dinucleotides TT, TC, TG, CT, CC, CG, AC, AA, AG, GT, GG, dinucleotides TC, TG, CC, AC, AG, GC, GG and dinucleotides TT, TC, TG, CT, CA, AC, AA, AG, GT, GA, GC respectively.

As for the first series of dinucleotides, it is expecially considered the case in which they are mixtured in four mixtures as follows: W=TC; TG; CC; AC; AA; X=TG; CG; AC; AG; GT; Y=TT; CT; AC; AA; GT; Z=TC; CT; AC; GT; GG;, and that in which codons are obtained on the our resin columns according to the following grouping:

AW$_1$=Isoleucine, Methionine, Threonine, Asparagine, Lysine;

CX$_1$=Leucine, Proline, Histidin, Glutamine, Arginine;

GY$_1$=Valine, Alanine, Aspartic Acid, Glutamic Acid, Glycine;

TZ$_1$=Phenylalanine, Serine, Tyrosine, Cysteine, Tryptophan.

Finally, it is considered of the same relevance the case where dinucleotides are mixtured among them in the following molar proportions: W$_2$: [AA]=[CC]=[TG]=[AC]=1 M, [TC]=1,5 M; X$_2$: [TG]=[AC]=[GT]=[CG]=1 M, [AG]=1,5 M; Y$_2$: [GT]=[AC]=[CT]=[AA]=1 M, and [TT]=1,5 M; Z$_2$: [GG]=2 M, [AC]=[CT]=[GT]=1 M and [TC]=1,5 M.

So far, only a general description of the present invention was given. With the aid of the examples hereinafter, a more detailed description of its specific embodiments aimed at providing a better understanding of aims, features, advantages and operation modalities of the invention will now be given. These examples are only given by way of illustration, and not for limitative purposes of the scope of the present invention, defined by the enclosed claims.

EXAMPLE 1

Synthesis of 11 protected dinucleotides according to the formulas described in FIG. 1.

In order to prepare the dimers necessary for the synthesis of a polynucleotide having a partially randomized (but controlled, for a better transcription in E.Coli) sequence, from the examination of Table IV the decision was made to prepare 11 dinucleotides shown hatched in the table, according to the method described by Kumar G. and Poonian (Kumar G. and Poonian M. S. J. Org. Chem. (1984), Vol 49, pp 4905–4912). Dimers thus obtained are protected at their 5'-terminus by a dimethoxytrityl group, while the 3' part of the dimer is derivatized with cyanoethylphosphoramidite. Bases are protected with the protective groups in use in the synthesis of the oligonucleotides according to the phosphoramidite method, as reported in Koomar and Poonian and specified in FIG. 1.

Dimers purity determined with TLC and 31P-NMR was inferred from the following list of analytical data:

1H-NMR(CDCl$_3$) common to all dimers: δ 1.15–1.25 (12H, m, isopropyl), 2.15–2.50 (4×2'-H), 2.80–2.90 (2H, m, —CH$_2$CN and 2H, n, OCH$_2$ cyanoethyl), 3.70–3.90 (13H, m,2×5'-H of 5' nucleoside, 2×OCH$_3$ of DMTr, POCH$_3$ and 2H, m, —CH-isopropyl), 4.00–4.50 (4H, 2×5'-H of 3' nucleoside and 2×4'-H), 5.00–5.35 (2H, m, 3'-H), 6.20–6.50 (2H, m, 1'H), 6.80–6.95 (4H, d, J=8.8 Hz, 3,3', 5,5'-H of DMTr), 7.15–7.30 (9H of DMTr); DMTr T/T Phos; $^1$H(CDCl$_3$): δ 1.90–1.95 (6H, m, CH$_3$ of Tim.), 7.20–7.25 (2H, m, 6-H of Tim.). $^{31}$P (CDCl$_3$): δ –1.41, –2.26 (2×P(V) diast.); 147.00, 148.60 (2×P(III) diast.). ESI-MS: m/z 1085.03 (M+Na$^+$); Rf: 0.44 (5% MeOH/DCM); DMTr A/A Phos; $^1$H(CDCl$_3$): δ 7.20–8.05 (10H, m, bz), 8.10–8.80 (4H, m, 2-H and 8-H of Ade). $^{31}$P (CDCl$_3$): δ –1.69, –1.91 (2×P(V) diast.); 148.10, 148.60 (2×P(III) diast.). ESI-MS: m/z 1289.5 (M+Na$^+$), Rf: 0.47 (5% MeOH/DCM); DMTr C/C Phos; $^1$H(CDCl$_3$): δ 7,25–7.40 (4H, m, 2×5,6-H of Cit.), 7.50–8.20 (10H, m, bz.). $^{31}$P (CDCl$_3$): δ –1.19, –1.94 (2×P(V) diast.); 147.88, 149.07 (2×P(III) diast.). ESI-MS: m/z 1242.5 (M+H$^+$); Rf: 0.48 (5% MeOH/DCM); DMTr G/G Phos; $^1$H(CDCl$_3$): δ 1.20–1.40 (12H, m, CH$_3$ of isobut), 2.40–2.55 (2H, m, CH of isobut), 7.50–7.60 (2H, m, 8-H of Gua). $^{31}$P (CDCl$_3$): δ –2.19, –1.51 (2×P(V) diast.); 147.69, 148.19 (2×P(III) diast). ESI-MS: mn/z 1253.2 (M+H$^+$); Rf: 0, 37 (5% MeOH/DCM); DMTr T/CPhos; $^1$H(CDCl$_3$): δ 1.20–1.40 (3H, m, CH$_3$ of Tim.), 7.30–7.40 (3H, m, 5,6 of Cit. and 6-H of Tim.), 7.45–8,20 (5H, m, bz). $^3$ P (CDCl$_3$): δ 1.00, –1.98 (2×P(V) diast.); 147.8, 148.4 (2×P(III)diast.). ESI-MS: m/z 1152.4 (M+H$^+$); Rf: 0.41 (5% MeOH/DCM); DMTr T/GPhos; $^1$H(CDCl$_3$): δ 1.05–1.15 (6H, m, CH$_3$ of isobut), 1.20–1.30 (3H, m, CH$_3$ of Tim.), 2.30–2,45 (1H, m, CH of isobut), 7.20–7.25 (1H, m, 6-H of Tim.), 7.40–7.70 (1H, m, 8-H of Gua). $^{31}$P (CDCl$_3$): δ –2.20, –3.00 (2×P(V) diast.); 147.20, 148.20 (2×P(III) diast.). ESI-MS: m/z 1158.4 (M+H$^+$); Rf: 0.37 (5% MeOH/DCM); DMTr A/G Phos; $^1$H(CDCl$_3$): δ 1.05–1.15 (6H, m, CH$_3$ of isobut), 2.30–2.50 (1H, m, CH of isobut), 7.45–8.70 (8H, m, 2,3,4,5,6-H di bz, 8-H of Gua and 2, 8-H of Ade). $^{31}$P (CDCl$_3$): δ –1.63, –2.20 (2×P(V) diast.); 147.06, 148.54 (2×P (III) diast.). ESI-MS: m/z 1271.4 (M+H$^+$); Rf: 0.38 (5 % MeOH/DCM); DMTr A/C Phos. $^1$H (CDCl$_3$): δ 7.05–7.15 (2H, m, 5,6-H of Cit.), 7.50–8.70 (12H, m, 2×(2,3,4,5,6-H) of bz and 2,8-H of Ade). $^{31}$P (CDCl$_3$): δ –0.19, 0.29 (2×P(V) diast.); 147.66, 148.66, 148.85 (2×P(III) diast.). ESI-MS: m/z 1266.1 (M+H$^+$); Rf: 0.44 (5% MeOH/DCM); DLMTr C/T Phos. $^1$H(CDCl$_3$): δ 1.40 (3H, s, 3H of Tm.), 7.20–7.40 (3H, m, 5,6-H of Cit and 6-H of Tim.), 7.50–8.05 (5H, m, bz). $^{31}$P (CDCl$_3$): δ –1.53, –1.98 (2×P (V) diast.); 148.20–148.45 (2×P(III) diast.). ESI-MS: m/z 1175 (M+Na$^+$); 1191 (M+K+); Rf: 0.42 (5% MeOH/DCM); DMTr G/T Phos. $^1$H(CDCl$_3$) δ 1.1–1.25 (6H, m, CH$_3$ of isobut), 1.30–1.35 (3H, m, CH$_3$ of Tim), 2.25–2.50 (1H, m, CH of isobut) 7.15–7.20 (1H, m, 6-H of Tim.), 7.70–7.75 (1H, m, 8-H of Gua). $^{31}$P (CDCl$_3$): δ –0.40, –1.00 (2×P(V) diast.); 148.00, 148.80 (2×P(III) diast.) ESI-MS: m/z 1158.5 (M+H$^+$); 1181 (M+Na$^+$); 1196.4 (M+K$^+$); 0.41 (5% MeOH/DCM); DMTr C/G Phos. $^1$H(CDCl$_3$): δ 1.30 (6H, m, CH$_3$ of isobut), 2.20–2.25 (1H, m, CH of isobut), 7.15–7.25 (2H, m, 5,6-H of Cit) 7.45–8.30 (6H, m, 5H Bz and 8-H of Gua). $^{31}$P (CDCl$_3$): δ –2,47, –2.69 (2×P(V) diast.); 147.75, 148.16 (2×P(III) diast.). ESI-MS: m/z 1246 (M+H$^+$); 0.44 (5% MeOH/DCM);

From this data it can be inferred that the synthetized dimers purity is of between 85 and 90%.

EXAMPLE 2

Synthesis of an oligonucleotide consisting of 20 nucleotides according to the formula:

5' -A GTC GCG [P' P] TCG ACC T-3' (SEQ ID NO:1)

where for P' and P are meant trinucleotides that may code for anyone of the twenty natural amino acids, selected to reflect the known use frequency for micro-organism E. Coli.

The mixture resulting from this synthesis will actually be constituted of a total of 400 different polynucleotides.

With the 11 dinucleotides prepared as for example 1, four mixtures are then prepared in the following way:

| Mixture Z | | |
|---|---|---|
| Dimer | TC | 0.0225 mmoles |
| | CT | 0.015 mmoles |
| | AC | 0.015 mmoles |
| | GT | 0.015 mmoles |
| | GG | 0.03 mmoles | the weighted amounts are then dissolved in 1 ml acetonitrile to give a final concentration of 0,0975 mmoles/ml (i.e. 0,0975 M)

| Mixture X | | |
|---|---|---|
| Dimer | TG | 0.015 mmoles |
| | CG | 0.015 mmoles |
| | AC | 0.015 mmoles |
| | AG | 0.0225 mmoles |
| | GT | 0.015 mmoles |

The weighted amounts are dissolved in 1 ml acetonitrile to give a final concentration of 0,0825 mmoles/ml (i.e. 0,0825 M)

| Mixture W | | |
|---|---|---|
| Dimer | TC | 0.0225 mmoles |
| | TG | 0.015 mmoles |
| | CC | 0.015 mmoles |
| | AC | 0.015 mmoles |
| | AA | 0.015 mmoles |

The weighted amounts are dissolved in 1 ml acetonitrile to give a final concentration of 0,0825 mmoli/ml (i.e. 0,0825 M)

| Mixture Y | | |
|---|---|---|
| Dimers | TT | 0.0225 mmoles |
| | CT | 0.015 mmoles |
| | AC | 0.015 mmoles |
| | AA | 0.015 mmoles |
| | GT | 0.015 mmoles |

The weighted amounts are dissolved in 1 ml acetonitrile to give a final concentration of 0,0825 mmoles/ml (i.e. 0,0825 M).

The four mixtures (W, X, Y, Z) are solubilzed in acetonitrile containing less than 30 ppm water and in Argon, loaded onto the DNA APPLIED BIOSYSTEM* 394 DNA/RNA synthesizer respectively in positions 5, 6, 7, 8 of the machine. All reagents (solvents, activators, and synthesis columns on 40 nmoles scale) were bought from PERKIN ELMER, and used in accordance to the maker instructions.

The synthesis starts with the synthesis in parallel on the 4 columns of the 3' part of the oligonucleotide:

```
Column 1      TCG ACC T      -3'
Column 2      TCG ACC T      -3'
Column 3      TCG ACC T      -3'
Column 4      TCG ACC T      -3'
```

Then the degenerated portion of the oligonucleotide is synthetized as aforedescribed:

on columns 1, 2, 3, and 4, dimer mixtures W, X, Y e Z in the aforespecified concentrations are additioned and the reaction is carried out allowing for a 3-minuses coupling time. The condensing reaction of the dimers is usually carried out with a 90–95% yield, measured with trityl release. On the columns the following oligonucleotides are synthetized:

| Column 1 | W TCG ACC T | -3' |
| Column 2 | X TCG ACC T | -3' |
| Column 3 | Y TCG ACC T | -3' |
| Column 4 | Z TCG ACC T | -3' |

Then the addition of bases A, C, G and T follows, respectively onto reaction columns 1, 2, 3 and 4:

| Column 1 | AW TCG ACC T | -3' | (SEQ ID NO:2) |
| Column 2 | CX TCG ACC T | -3' | (SEQ ID NO:3) |
| Column 3 | GY TCG ACC T | -3' | (SEQ ID NO:4) |
| Column 4 | TZ TCG ACC T | -3' | (SEQ ID NO:5) |

After the usual acetylation and oxidation reactions (in accordance with the classical synthesis processes), the synthesis is stopped. The columns are disassembled, opened, and resin of the four synthesis columns is unified (for a total of 40 mg) and mixtured homogeneously.

The mixture is then redivided into four equal parts (4×10 mg) and is then redivided again into four new synthesis columns:

| Column 1 | P TCG ACC T | -3' | (SEQ ID NO:6) |
| Column 2 | P TCG ACC T | -3' | (SEQ ID NO:6) |
| Column 3 | P TCG ACC T | -3' | (SEQ ID NO:6) |
| Column 4 | P TCG ACC T | -3' | (SEQ ID NO:6) | where P=(AW+CX+GY+TZ).

The process is repeated for the second degenerated position: P'

The mixtures W, X, Y, Z are respectively additioned to columns 1, 2, 3 e 4:

| Column 1 | W P TCG ACC T | -3' | (SEQ ID NO:7) |
| Column 2 | X P TCG ACC T | -3' | (SEQ ID NO:8) |
| Column 3 | Y P TCG ACC T | -3' | (SEQ ID NO:9) |
| Column 4 | Z P TCG ACC T | -3' | (SEQ ID NO:10) | then the addition of the third codon base onto the respective columns follows:

| Column 1 | AW | P | TCG ACC T | -3' | (SEQ ID NO:11) |
| Column 2 | CX | P | TCG ACC T | -3' | (SEQ ID NO:12) |
| Column 3 | GY | P | TCG ACC T | -3' | (SEQ ID NO:13) |
| Column 4 | TZ | P | TCG ACC T | -3' | (SEQ ID NO:14) |

Then the resin of the four columns is homogeneously mixtured and is subdivided in four new synthesis columns. At this point the second degenerated codon P' was synthetized, therefore the columns contain:

```
Column 1  P' P TCG ACC T  -3'  (SEQ ID NO:15)
Column 2  P' P TCG ACC T  -3'  (SEQ ID NO:15)
Column 3  P' P TCG ACC T  -3'  (SEQ ID NO:15)
Column 4  P' P TCG ACC T  -3'  (SEQ ID NO:15)
``` where P'=P=(AW, CX, GY, TZ)

After the synthesis of the second trinucleotide P'0 (base+dimer mixture), the 5' region flanking he oligonucleotide [AGT CGC G] is synthetized onto the four columns in parallel, constituting therefore the sequence oligonucleotide:

5'-AGT CGC G P' P TCG ACC T-3' (SEQ ID NO:1)

where P'=P=(AW, CX, GY, TZ) corresponding to codons: ATC, ATG, ACC, AAC, AAA, CTG, CCG, CAC, CCG, CGT, GTT, GCT, GAC, GAA, GGT, TTC, TCT, TAC, TGT e TGG.

When the synthesis is completed the oligomer sticking to the resin used for the synthesis is removed and deprotected in accordance with the classical processes adopted for the construction of synthetic oligonucleotides using the chemistry of 0-methyl phosphoramidites (7).

EXAMPLE 3

Functional and genetic analysis of the polynucleotide synthetized in Example 2, having the sequence:

5'-A GTC GCG [P' P] TCG ACC T-3' (SEQ ID NO:1)

where P'=P=(AW, CX, GY, TZ) corresponding to codons: ATC, ATG, ACC, AAC, AAA, CTG, CCG, CAC, CAC, CGT, GTT, GCT, GAC, GAA, GGT, TTC, TCT, TAC, TGT e TGG.

The degenerated polynucleotide synthetized in the example 2 is made of a mixture of 400 polynucleotides. In the present example this mixture was named for convenience "polynucleotide B". In order to analyze its real composition, to verify in practice that all of the 400 molecular species expected of the synthesis are present in the mixture, the following steps were taken:

→ the following oligonucleotide was synthetized with a conventional method:
oligonucleotide A
14 nucleotides
sequence: 5° CGCGACT AGGTCGA3' (SEQ ID NO:16).

The sequence of this oligonucleotide as designed to be complementary both in its 3'-terminus part (7 nucleotides) with the 3'-terminus part of the oligonucleotide B, and in its 5'-end part (7 nucleotides) with the 5'-terminus part of the oligonucleotide B.

```
seq. (A)=5'CGCGACTA AGG TCG A    3'                    (SEQ ID NO:17)
seq. (B)=5'         TCC AGC T [P P']GCGCTG A 3'        (SEQ ID NO:18)
seq. (A)=5'                         CGCGAC T AGGTCGA3' (SEQ ID NO:16)
```

→ Both oligonucleotides were enzymatically phosphorylated at 5'-terminus, mixtured in equimolar amounts, denaturated at 95° C. and then left anilating and polymerizing bringing temperature slowly at 15° C.

→ The mixture then underwent enzymatic ligation, and then a completing reaction by incubation with Klenow polymerase. The ligating reaction entails the formation of a double helix DNA fragment containing serial "bead-tail" repetitions of a DNA unit constituted by the two coupled oligonucleotides A and B.

→ The generated fragments, resulting with blunt ends, were then cloned in the EcoRV site of the pBSks+ plasmide. The ligation mixture was subsequently enriched for the recombinant clones with EcoRV digestion, and used to transform competent XL-1 blue bacterial cells.

→ Recombinant clones were identified with colorimetrical selection onto LB+Amp+Xgal/IPTG plates.

→ 20 randomly selected clones were expanded, and the entire recombinant sequence therein contained was amplified and cloned with PCR (Polimerase Chain Reaction).

→ The analysis with elettrophoresis on agarose gel allowed the determining of the length of each clone insertion.

→ Inserts of 20 clones were sequenced, thus allowing the determining of 170 variable portions comprised in oligonucleotide B.

Table VIII shows frequences observed for each of the 20 trinucleotides provided for by the experimental design. From Table VIII it results that all of the trinucleotides expected in the experimental design (according to Table IV) are present, and that their frequency does not stand out in a significant way from an uniform distribution.

TABLE VII frequences of the triplets observed from the sequencing of 170 codons present in the degenerated portion of the DNA of 20 clones randomly selected in a library of degenerated oligonucleotides, synthetized with the method of the invention.

| CODONS | FREQUENCY |
|---|---|
| AAA | 11 |
| ACC | 7 |
| ATC | 11 |
| ATG | 7 |
| AAC | 7 |
| CTG | 12 |
| CAG | 13 |
| CAC | 11 |
| CGT | 7 |
| CCG | 5 |
| GTT | 14 |
| GAA | 11 |
| GAC | 11 |
| GCT | 5 |
| GGT | 3 |
| TGG | 6 |
| TTC | 6 |
| TAC | 10 |
| TCT | 10 |
| TGT | 3 |
| | 170 |

BIBLIOGRAPHICAL REFERENCES

Gait M. J., Oligonucleotides Synthesis "A Practical Approach Series". (1984) IRL Press Oxford Washington D.C.

Huang, W and Santi, D. V. (1994) Anal. Biochem. 218 pag. 454–457.

Kayushin A. L., Korosteleva M. D., Miroshnikov A. I., Kosch W., Zubov D. and Piel N. (1996) Nucleic Acid Research vol. 24, No 19, pages 3748–3755.

Kumar G. and Poonian M. S. J. Org. Chem. (1984), Vol. 49, pag. 4905–4912.

Lyttle M. H., Napolitano E. W., Calio B. L. and Kauvar L. M., Biotechniques (1995), Vol. 19; N 2, pag. 274–280.

Ono A., Matsuda A., Zhao J. and Santi D. V., Nucleic Acids Research (1995), Vol. 23, N22, pages 4677–4682.

Sambrook, J., Fritsch, E. F., and Maniatis, T. (1989) in "Molecular Cloning. A Laboratory Manual", Cold Spring Harbor Laboratory, 2nd edition Cold Spring Harbor, N.Y.

Virnekas B., Ge L., Plucksthun A., Schneider K. C., Wellnhofer G. and Moroney S. E., Nucleic Acids Research (1994), Vol. 22; N25, pag. 5600–5607.

I claim:

1. A process for the chemical synthesis of a polynucleotide having a totally or partially random sequence, said random sequence being constituted by trinucleotide sequence units coding for amino acids according to the degeneracy of the genetic code, wherein said polynucleotide is synthesized by:

a) utilizing a pre-synthesized mononucleotide and a pre-synthesized dinucleotide as a monomeric synthesis unit, said mononucleotide and dinucleotide being a sequence unit of said trinucleotide sequence units;

b) carrying out the synthesis of said polynucleotide on at least one support, wherein, on said support, first reaction cycles, in which a mixture of said dinucleotides is bound, are alternated with second reaction cycles in which one mononucleotide is bound, and wherein at least one alternation between the first and second reaction cycle is predefined in order to form trinucleotide sequence units with a reduced number of mononucleotide and dinucleotide sequence units relative to the mononucleotide and dinucleotide sequence units forming said trinucleotide sequence units according to the genetic code, thereby reducing the degeneracy effects of the genetic code; and c) repeating step b) until said polynucleotide is of desired length.

2. The process for the chemical synthesis of polynucleotides according to claim 1, wherein said synthesis is carried out on at least two supports.

3. The process for the chemical synthesis of polynucleotides according to claim 2, wherein following the synthesis of a trinucleotide unit the supports are mixtured and then divided in at least two supports.

4. The process for the chemical synthesis of polynucleotides according to claim 1, wherein said dinucleotides constitute the second and the third base, of the trinucleotide units that share the first base.

5. The process for the chemical synthesis of polynucleotides according to claim 4, comprising the following steps:

a) preselecting the dinucleotides in groups, each group being composed of at least one of those dinucleotides that constitute the second and the third base of at least one of the trinucleotide units that are to be present in the sequence, and that share the first base;

b) preparing mixtures containing activated and protected dinucleotides, said activated and protected dinucleotides being distributed in said mixtures, as preselected by the step under a), in a concentration suitable to obtain homogeneity in the corresponding trinucleotide units representation;

c) synthesising a polynucleotide having a known sequence on supports for solid phase synthesis included in containers;

d) adding the mixtures containing activated and protected dinucleotides under b) to the synthesis supports, one for each support, and performing a binding reaction between the activated and protected dinucleotides, and the 5'-terminus of the synthesised polynucleotide under c);

e) adding at least one activated and protected mononucleotide to at least one of the synthesis supports, one mononucleotide for each support, and performing binding reaction between said activated and protected mononucleotide and the 5'-terminus of the dinucleotides bound to the synthesised polynucleotide under c) according to step d);

f) opening the containers and mixturing the supports in order to obtain a homogeneous reaction mixture;

g) reconstituting the synthesis supports with an amount of said homogeneous reaction mixture, equal to a 1/n fraction for each support, n being the number of supports used;

h) repeating the steps under d), e) and f), as many times as required by the experimental design;

i) synthesising on the 5'-terminus of the polynucleotide thus obtained a polynucleotide having a known sequence.

6. The process for the chemical synthesis of polynucleotides according to claim 1, wherein said dinucleotides constitute the first and the second base, of the trinucleotide units that share the third base.

7. The process for the chemical synthesis of polynucleotides according to claim 6, comprising the following steps:

$a_1$) preselecting the dinucleotides in groups, each group being composed of at least one of those dinucleotides that constitute the first and the second base of at least one of the trinucleotide units that are to be present in the sequence, and that shore the third base;

$b_1$) preparing mixtures containing activated and protected dinucleotides, said activated and protected dinucleotides being distributed in said mixtures, as preselected by the operation under $a_1$), in a concentration suitable to obtain homogeneity in the corresponding trinucleotide units representation;

$c_1$) synthesising a polynucleotide having a known sequence on synthesis supports for solid phase synthesis included in containers;

$d_1$) adding at least one activated and protected mononucleotide to at least one of the synthesis supports, one mononucleotide for each support, and performing a binding reaction between the activated and protected mononucleotides, and the 5'-terminus of the synthesised polynucleotide under $c_1$);

$e_1$) adding the mixtures containing activated and protected dinucleotides under $b_1$) to the synthesis supports, one for each support, and performing binding reaction between said activated and protected dinucleotide and the 5'-terminus of the mononucleotides bound to the synthesised polynucleotide under $c_1$) according to step $d_1$);

$f_1$) opening the containers and mixturing the supports in order to obtain a homogeneous reaction mixture;

$g_1$) reconstituting the synthesis supports with an amount of said homogeneous reaction mixture, equal to a 1/n fraction for each support, n being the number of supports used;

$h_1$) repeating the steps under $d_1$), $e_1$) and $f_1$), as many times as required by the experimental design;

$i_1$) synthesising on the 5'-terminus of the polynucleotide thus obtained a polynucleotide having a known sequence.

8. The process for the chemical synthesis of polynucleotide sequences according to claim 1, wherein said synthesis is carried in parallel.

9. The process for the chemical synthesis of polynucleotide sequences according to claim 1, wherein the dinucleotide mixtures and the synthesis supports are four.

10. The process for the chemical synthesis of polynucleotide sequences according to claim 1, wherein said supports are resin supports.

11. The process for the chemical synthesis of polynucleotide sequences according to claim 1, wherein said containers are columns.

12. The process for the chemical synthesis of polynucleotides according to claim 1, wherein said mononucleotide and dinucleotide are deoxyribonucleotides and the trinucleotide units are codons.

13. The process for the chemical synthesis of polynucleotides according to claim 1, wherein said mononucleotide and dinucleotide are ribonucleotides the trinucleotide units are anticodons.

14. The process for the chemical synthesis of polynucleotide sequences according to claim 1, wherein the dinucleotides are preselected to form trinucleotide units corresponding to the most frequent codons in *Escherichia Coli* genoma.

15. The process for the chemical synthesis of polynucleotide sequences according to claim 14 when depending on claim 12, wherein said dinucleotides are TT, TC, TG, CT, CC, CG, AC, AA, AG, GT, and GG.

16. The process for the chemical synthesis of polynucleotide sequences according to claim 15, wherein said dinucleotides are mixtured in four mixtures as follows:

W=TC; TG; CC; AC; AA;

X=TG; CG; AC; AG; GT;

Y=AA; AC; CT; GT; TT;

Z=GG; AC; CT; GT; TC.

17. The process for the chemical synthesis of polynucleotide sequences according to claim 16, wherein codons are obtained on synthesis supports to code for amino acids according to the following grouping:

$AW_1$=Isoleucine, Methionine, Threonine, Asparagine, Lysine;

$CX_1$=Leucine, Proline, Histidin, Glutamine, Arginine;

$GY_1$=Valine, Alanine, Aspartic Acid, Glutamic Acid, Glycine;

$TZ_1$=Phenylalanine, Serine, Tyrosine, Cysteine, Tryptophan.

18. The process for the chemical synthesis of polynucleotide sequences according to claim 17, wherein dinucleotides are intermixtured in the following proportions.

$W_2$: [AA]=[CC]=[TC]=[AC]=1 M, and [TG]=1,5 M;

$X_2$: [TG]=[AC]=[GT]=[CG]=1 M, and [AG]=1,5 M;

$Y_2$: [GT]=[AC]=[CT]=[AA]=1 M, and [TT]=1,5 M;

$Z_2$: [GG]=2 M, [AC]=[CT]=[GT]=1 M and [TC]=1,5 M.

19. The process for the chemical synthesis of polynucleotide according to claim 1, wherein the dinucleotides are preselected to form trinucleotide units corresponding to the most frequent codons in eucaryotic organisms genomas.

20. The process for the chemical synthesis of polynucleotide sequences according to claim 19, when depending on claim 12, wherein said dinucleotides are TC, TG, CC, AC, AG, GC, and GG.

21. The process for the chemical synthesis of polynucleotide sequences according to claim 19, wherein said eucaryotic organisms are Yeasts.

22. The process for the chemical synthesis of polynucleotide sequences according to claim 21 when depending on claim 12, wherein said dinucleotides are TT, TC, TG, CT, CA, AC, AA, AG, GT, GA, and GG.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Randomly generated sequences.
<223> OTHER INFORMATION: N at position 8 is A, T, C, or G.
     When N at position 8 is A, then N at position 9 is
     T, A, or C.  When N at position 8 is A, and N at
     position 9 is T, then N at position 10 is C or G.
<223> OTHER INFORMATION: When N at position 8 is A, and N at position 9
     is C, then N at position 10 is C.
     When N at position 8 is A, and N at position 9 is
     A, then N at position 10 is C or A.
<223> OTHER INFORMATION: When N at position 8 is C, then N at position 9
     is T, C, A, or G.
     When N at position 8 is C, and N at position 9 is
     T, then N at position 10 is G.
<223> OTHER INFORMATION: When N at position 8 is C, and N at position 9
     is C, then N at position 10 is G.
     When N at position 8 is C, and N at position 9 is
     A, then N at position 10 is C or G.
<223> OTHER INFORMATION: When N at position 8 is C, and N at position 9
     is G, then N at position 10 is T.
     When N at position 8 is G, and N at position 9 is
     T, then N at position 10 is T.
<223> OTHER INFORMATION: When N at position 8 is G, and N at position 9
     is C, then N at position 10 is T.
     When N at position 8 is G, and N at position 9 is
     A, then N at position 10 is C or A.
<223> OTHER INFORMATION: When N at position 8 is G, and N at position 9
     is G, then N at position 10 is T.
     When N at position 8 is T, and N at position 9 is
     T, then N at position 10 is C.
```

<223> OTHER INFORMATION: When N at position 8 is T, and N at position 9
is C, then N at position 10 is T.
When N at position 8 is T, and N at position 9 is
A, then N at position 10 is C.
<223> OTHER INFORMATION: When N at position 8 is T, and N at position 9
is G, then N at position 10 is T or G.  N at position
11 is A, T, C, or G.  When N at position 11 is A,
then N at position 12 is T, A, or C.
<223> OTHER INFORMATION: When N at position 11 is A, and N at position
12 is T, then N at position 13 is C or G.
When N at position 11 is A, and N at position 12
is C, then N at position 13 is C.
<223> OTHER INFORMATION: When N at position 11 is A, and N at position
12 is A, then N at position 13 is C or A.
When N at position 11 is C, then N at position 12
is T, C, A, or G.
<223> OTHER INFORMATION: When N at position 11 is C, and N at position
12 is T, then N at position 13 is G.
When N at position 11 is C, and N at position 12
is C, then N at position 13 is G.
<223> OTHER INFORMATION: When N at position 11 is C, and N at position
12 is A, then N at position 13 is C or G.
When N at position 11 is C, and N at position 12
is G, then N at position 13 is T.
<223> OTHER INFORMATION: When N at position 11 is G, and N at position
12 is T, then N at position 13 is T.
When N at position 11 is G, and N at position 12
is C, then N at position 13 is T.
<223> OTHER INFORMATION: When N at position 11 is G, and N at position
12 is A, then N at position 13 is C or A.
When N at position 11 is G, and N at position 12
is G, then N at position 13 is T.
<223> OTHER INFORMATION: When N at position 11 is T, and N at position
12is T, then N at position 13 is C.
When N at position 11 is T, and N at position 12
is C, then N at position 13 is T.
<223> OTHER INFORMATION: When N at position 11 is T, and N at position
12 is A, then N at position 13 is C.
When N at position 11 is T, and N at position 12
is G, then N at position 13 is T or G.

<400> SEQUENCE: 1
agtcgcgnnn nnntcgacct                                            20

<210> SEQ ID NO 2
<211> LENGTH: 10
<212> TYPE: DNA
<213> ORGANISM: Artificial Sequence
<220> FEATURE:
<223> OTHER INFORMATION: Randomly generated sequences.
<223> OTHER INFORMATION: N at position 2 is T, C, or A.
When N at position 2 is T, then N at position 3 is
C or G.
<223> OTHER INFORMATION: When N at position 2 is C, then N at position 3
is C.
When N at position 2 is A, then N at position 3 is
C or A.

<400> SEQUENCE: 2 anntcgacct                                                       10

<210> SEQ ID NO 3
<211> LENGTH: 10
<212> TYPE: DNA
<213> ORGANISM: Artificial Sequence
<220> FEATURE:
<223> OTHER INFORMATION: Randomly generated sequences.
<223> OTHER INFORMATION: N at position 2 is T, C, A, or G.
<223> OTHER INFORMATION: When N at position 2 is T, then N at position 3
is G.
When N at position 2 is C, then N at position 3 is
C.
<223> OTHER INFORMATION: When N at position 2 is A, then N at position 3
is C or G.
When N at position 2 is G, then N at position 3 is -continued

T.

<400> SEQUENCE: 3 cnntcgacct                                                             10

<210> SEQ ID NO 4
<211> LENGTH: 10
<212> TYPE: DNA
<213> ORGANISM: Artificial Sequence
<220> FEATURE:
<223> OTHER INFORMATION: Randomly generated sequences.
<223> OTHER INFORMATION: N at position 2 is T, C, A, or G.
<223> OTHER INFORMATION: When N at position 2 is T, N at position 3 is
     T. When N at position 2 is C, N at position 3 is T.
<223> OTHER INFORMATION: When N at position 2 is A, N at position 3 is C
     or A.
     When N at position 2 is G, N at position 3 is T.

<400> SEQUENCE: 4 gnntcgacct                                                             10

<210> SEQ ID NO 5
<211> LENGTH: 10
<212> TYPE: DNA
<213> ORGANISM: Artificial Sequence
<220> FEATURE:
<223> OTHER INFORMATION: Randomly generated sequences.
<223> OTHER INFORMATION: N at position 2 is T, C, A, or G.
<223> OTHER INFORMATION: When N at position 2 is T, N at position 3 is
     C. When N at position 2 is C, N at position 3 is T.
<223> OTHER INFORMATION: When N at position 2 is A, N at position 3 is
     C. When N at position 2 is G, N at position 3 is T or
     G.

<400> SEQUENCE: 5 tnntcgacct                                                             10

<210> SEQ ID NO 6
<211> LENGTH: 10
<212> TYPE: DNA
<213> ORGANISM: Artificial Sequence
<220> FEATURE:
<223> OTHER INFORMATION: Randomly generated sequences.
<223> OTHER INFORMATION: N at position 1 is A, C, G, or T.
<223> OTHER INFORMATION: When N at position 1 is A, N at position 2 is
     the same as N at position 2 of SEQ ID NO 2, and N at
     position 3 is the same as N at position 3 of SEQ
     ID NO 2.
<223> OTHER INFORMATION: When N at position 1 is C, then N at position 2
     is the same as N at position 2 of SEQ ID NO 3, and N
     at position 3 is the same as N at position 3 of
     SEQ ID NO 3.
<223> OTHER INFORMATION: When N at position 1 is G, then N at position 2
     is the same as N at position 2 of SEQ ID NO 4, and N
     at position 3 is the same as N at position 3 of
     SEQ ID NO 4.
<223> OTHER INFORMATION: When N at position 1 is T, then N at position 2
     is the same as N at position 2 of SEQ ID NO 5, and N
     at position 3 is the same as N at position 3 of
     SEQ ID NO 5.

<400> SEQUENCE: 6 nnntcgacct                                                             10

<210> SEQ ID NO 7
<211> LENGTH: 12
<212> TYPE: DNA
<213> ORGANISM: Artificial Sequence
<220> FEATURE:
<223> OTHER INFORMATION: Randomly generated sequences.
<223> OTHER INFORMATION: N at position 1 is the same as N at position 2 of SEQ ID NO 2 and N at position 2 is the same as N
at position 3 of SEQ ID NO 3.
<223> OTHER INFORMATION: N at position 3 is the same as N at position 1
of SEQ ID NO 6.
<223> OTHER INFORMATION: N at position 4 is the same as N at position 2
of SEQ ID NO 6.
<223> OTHER INFORMATION: N at position 5 is the same as N at position 3
of SEQ ID NO 6.

<400> SEQUENCE: 7
nnnnntcgac ct                                                      12

<210> SEQ ID NO 8
<211> LENGTH: 12
<212> TYPE: DNA
<213> ORGANISM: Artificial Sequence
<220> FEATURE:
<223> OTHER INFORMATION: Randomly generated sequences.
<223> OTHER INFORMATION: N at position 1 is the same as N at position 2
of SEQ ID NO 3.
<223> OTHER INFORMATION: N at position 2 is the same as N at position 3
of SEQ ID NO 3.
<223> OTHER INFORMATION: N at position 3 is the same as N at position 1
of SEQ ID NO 6.
<223> OTHER INFORMATION: N at position 4 is the same as N at position 2
of SEQ ID NO 6.
<223> OTHER INFORMATION: N at position 5 is the same as N at position 3
of SEQ ID NO 6.

<400> SEQUENCE: 8
nnnnntcgac ct                                                      12

<210> SEQ ID NO 9
<211> LENGTH: 12
<212> TYPE: DNA
<213> ORGANISM: Artificial Sequence
<220> FEATURE:
<223> OTHER INFORMATION: Randomly generated sequences.
<223> OTHER INFORMATION: N at position 1 is the same as N at position 2
of SEQ ID NO 4.
<223> OTHER INFORMATION: N at position 2 is the same as N at position 3
of SEQ ID NO 4.
<223> OTHER INFORMATION: N at position 3 is the same as N at position 1
of SEQ ID NO 6.
<223> OTHER INFORMATION: N at position 4 is the same as N at position 2
of SEQ ID NO 6.
<223> OTHER INFORMATION: N at position 5 is the same as N at position 3
of SEQ ID NO 6.

<400> SEQUENCE: 9
nnnnntcgac ct                                                      12

<210> SEQ ID NO 10
<211> LENGTH: 12
<212> TYPE: DNA
<213> ORGANISM: Artificial Sequence
<220> FEATURE:
<223> OTHER INFORMATION: Randomly generated sequences.
<223> OTHER INFORMATION: N at position 1 is the same as N at position 2
of SEQ ID NO 5.
<223> OTHER INFORMATION: N at position 2 is the same as N at position 3
of SEQ ID NO 5.
<223> OTHER INFORMATION: N at position 3 is the same as N at position 1
of SEQ ID NO 6.
<223> OTHER INFORMATION: N at position 4 is the same as N at position 2
of SEQ ID NO 6.
<223> OTHER INFORMATION: N at position 5 is the same as N at position 3
of SEQ ID NO 6.

<400> SEQUENCE: 10
nnnnntcgac ct                                                      12

```
<210> SEQ ID NO 11
<211> LENGTH: 13
<212> TYPE: DNA
<213> ORGANISM: Artificial Sequence
<220> FEATURE:
<223> OTHER INFORMATION: Randomly generated sequences.
<223> OTHER INFORMATION: N at position 2 is the same as N at position 1
      of SEQ ID NO 7.
<223> OTHER INFORMATION: N at position 3 is the same as N at position 2
      of SEQ ID NO 7.
<223> OTHER INFORMATION: N at position 4 is the same as N at position 3
      of SEQ ID NO 7.
<223> OTHER INFORMATION: N at position 5 is the same as N at position 4
      of SEQ ID NO 7.
<223> OTHER INFORMATION: N at position 6 is the same as N at position 5
      of SEQ ID NO 7.

<400> SEQUENCE: 11
annnnntcga cct                                                      13

<210> SEQ ID NO 12
<211> LENGTH: 13
<212> TYPE: DNA
<213> ORGANISM: Artificial Sequence
<220> FEATURE:
<223> OTHER INFORMATION: Randomly generated sequences.
<223> OTHER INFORMATION: N at position 2 is the same as N at position 1
      of SEQ ID NO 8.
<223> OTHER INFORMATION: N at position 3 is the same as N at position 2
      of SEQ ID NO 8.
<223> OTHER INFORMATION: N at position 4 is the same as N at position 3
      of SEQ ID NO 8.
<223> OTHER INFORMATION: N at position 5 is the same as N at position 4
      of SEQ ID NO 8.
<223> OTHER INFORMATION: N at position 6 is the same as N at position 5
      of SEQ ID NO 8.

<400> SEQUENCE: 12
cnnnnntcga cct                                                      13

<210> SEQ ID NO 13
<211> LENGTH: 13
<212> TYPE: DNA
<213> ORGANISM: Artificial Sequence
<220> FEATURE:
<223> OTHER INFORMATION: Randomly generated sequences.
<223> OTHER INFORMATION: N at position 2 is the same as N at position 1
      of SEQ ID NO 9.
<223> OTHER INFORMATION: N at position 3 is the same as N at position 2
      of SEQ ID NO 9.
<223> OTHER INFORMATION: N at position 4 is the same as N at position 3
      of SEQ ID NO 9.
<223> OTHER INFORMATION: N at position 5 is the same as N at position 4
      of SEQ ID NO 9.
<223> OTHER INFORMATION: N at position 6 is the same as N at position 5
      of SEQ ID NO 9.

<400> SEQUENCE: 13
gnnnnntcga cct                                                      13

<210> SEQ ID NO 14
<211> LENGTH: 13
<212> TYPE: DNA
<213> ORGANISM: Artificial Sequence
<220> FEATURE:
<223> OTHER INFORMATION: Randomly generated sequences.
<223> OTHER INFORMATION: N at position 2 is the same as N at position 1
      of SEQ ID NO 10.
<223> OTHER INFORMATION: N at position 3 is the same as N at position 2
      of SEQ ID NO 10.
<223> OTHER INFORMATION: N at position 4 is the same as N at position 3
      of SEQ ID NO 10.
```

```
<223> OTHER INFORMATION: N at position 5 is the same as N at position 4
      of SEQ ID NO 10.
<223> OTHER INFORMATION: N at position 6 is the same as N at position 5
      of SEQ ID NO 10.

<400> SEQUENCE: 14
tnnnnntcga cct                                                          13

<210> SEQ ID NO 15
<211> LENGTH: 13
<212> TYPE: DNA
<213> ORGANISM: Artificial Sequence
<220> FEATURE:
<223> OTHER INFORMATION: Randomly generated sequences.
<223> OTHER INFORMATION: N at position 1 is the same as N at position 1
      of SEQ ID NO 6.
<223> OTHER INFORMATION: N at position 2 is the same as N at position 2
      of SEQ ID NO 6.
<223> OTHER INFORMATION: N at position 3 is the same as N at position 3
      of SEQ ID NO 6.
<223> OTHER INFORMATION: N at position 4 is the same as N at position 1
      of SEQ ID NO 6.
<223> OTHER INFORMATION: N at position 5 is the same as N at position 2
      of SEQ ID NO 6.
<223> OTHER INFORMATION: N at position 6 is the same as N at position 3
      of SEQ ID NO 6.

<400> SEQUENCE: 15
nnnnnntcga cct                                                           3

<210> SEQ ID NO 16
<211> LENGTH: 14
<212> TYPE: DNA
<213> ORGANISM: Artificial Sequence
<220> FEATURE:
<223> OTHER INFORMATION: Randomly generated sequences.

<400> SEQUENCE: 16
cgcgactagg tcga                                                         14

<210> SEQ ID NO 17
<211> LENGTH: 15
<212> TYPE: DNA
<213> ORGANISM: Artificial Sequence
<220> FEATURE:
<223> OTHER INFORMATION: Randomly generated sequences.

<400> SEQUENCE: 17
cgcgactaag gtcga                                                        15

<210> SEQ ID NO 18
<211> LENGTH: 20
<212> TYPE: DNA
<213> ORGANISM: Artificial Sequence
<220> FEATURE:
<223> OTHER INFORMATION: Randomly generated sequences.
<223> OTHER INFORMATION: N at position 8 is the same as N at position 1
      of SEQ ID NO 6.
<223> OTHER INFORMATION: N at position 9 is the same as N at position 2
      of SEQ ID NO 6.
<223> OTHER INFORMATION: N at position 10 is the same as N at position 3
      of SEQ ID NO 6.
<223> OTHER INFORMATION: N at position 11 is the same as N at position 1
      of SEQ ID NO 6.
<223> OTHER INFORMATION: N at position 12 is the same as N at position 2
      of SEQ ID NO 6.
<223> OTHER INFORMATION: N at position 13 is the same as N at position 3
      of SEQ ID NO 6.

<400> SEQUENCE: 18
tccagctnnn nnngcgctga                                                   20
```